US009579052B2

(12) United States Patent
Halldorsson et al.

(10) Patent No.: US 9,579,052 B2
(45) Date of Patent: Feb. 28, 2017

(54) TEMPORAL OXIMETER

(75) Inventors: Gisli Hreinn Halldorsson, Reykjavik (IS); Robert Arnar Karlsson, Reykjavik (IS); Einar Stefansson, Reykjavik (IS); Sveinn Hakon Hardarson, Reykjavik (IS)

(73) Assignee: OXYMAP EHF., Reykjavik (IS)

( * ) Notice: Subject to any disclaimer, the term of this patent is extended or adjusted under 35 U.S.C. 154(b) by 1157 days.

(21) Appl. No.: 13/377,749

(22) PCT Filed: Jun. 11, 2010

(86) PCT No.: PCT/IS2010/050004
§ 371 (c)(1),
(2), (4) Date: Dec. 12, 2011

(87) PCT Pub. No.: WO2010/143208
PCT Pub. Date: Dec. 16, 2010

(65) Prior Publication Data
US 2012/0093389 A1 Apr. 19, 2012

(30) Foreign Application Priority Data
Jun. 12, 2009 (IS) .............................. 8831

(51) Int. Cl.
*G06K 9/00* (2006.01)
*A61B 5/1455* (2006.01)
(Continued)

(52) U.S. Cl.
CPC ...... *A61B 5/14555* (2013.01); *A61B 5/14535* (2013.01); *A61B 5/726* (2013.01)

(58) Field of Classification Search
CPC .................................................. A61B 5/14555
(Continued)

(56) References Cited
U.S. PATENT DOCUMENTS 5,413,098 A * 5/1995 Benaron ........................ 600/310
5,776,060 A * 7/1998 Smith et al. .................. 600/340
(Continued)

OTHER PUBLICATIONS

H. Narasimha-lyer et al., "Algorithms for automated oximetry along the retinal vascular tree from dual-wavelength fundus images", Oct. 2005, Journal of Biomedical Optics vol. 10(5), p. 1-15.*

(Continued)

*Primary Examiner* — Gandhi Thirugnanam
(74) *Attorney, Agent, or Firm* — Birch, Stewart, Kolasch & Birch, LLP

(57) ABSTRACT

A method and an apparatus for detecting change in retinal oxygen saturation over time are provided. The method includes the steps of capturing a first group of images of two or more wavelengths, calculating oxygen saturation of a vessel in the first group of images, storing the first group of images on a data storage device, capturing a second group of images of two or more wavelengths, calculating the oxygen saturation of a vessels in the second group of images, storing the second group of images on a data storage device, spatially registering the pair of the group of images, captured at different time and calculate the change in oxygen saturation. The method also includes means to validate whether an observed change in oxygen saturation is a real physiological change or artificial.

19 Claims, 7 Drawing Sheets

(51) Int. Cl.
  *A61B 5/145* (2006.01)
  *A61B 5/00* (2006.01)

(58) Field of Classification Search
  USPC .................. 382/134; 600/323, 340; 351/206
  See application file for complete search history.

(56) References Cited

U.S. PATENT DOCUMENTS

| | | | |
|---|---|---|---|
| 6,053,865 A * | 4/2000 | Sugiyama et al. | 600/300 |
| 6,198,532 B1 * | 3/2001 | Cabib et al. | 356/456 |
| 6,244,712 B1 * | 6/2001 | Smith et al. | 351/221 |
| 6,276,798 B1 * | 8/2001 | Gil et al. | 351/206 |
| 6,285,780 B1 * | 9/2001 | Yamakita et al. | 382/110 |
| 6,569,104 B2 * | 5/2003 | Ono et al. | 600/504 |
| 6,728,561 B2 * | 4/2004 | Smith et al. | 600/323 |
| 7,134,754 B2 * | 11/2006 | Kerr et al. | 351/206 |
| 7,676,253 B2 * | 3/2010 | Raridan, Jr. | 600/344 |
| 7,774,036 B2 * | 8/2010 | Halldorsson | A61B 3/1241 600/323 |
| 8,224,425 B2 * | 7/2012 | Freeman et al. | 600/473 |
| 8,403,862 B2 * | 3/2013 | Grinvald et al. | 600/558 |
| 8,441,530 B2 * | 5/2013 | Radeva et al. | 348/77 |
| 2004/0156016 A1 * | 8/2004 | Kerr et al. | 351/206 |
| 2006/0276698 A1 * | 12/2006 | Halldorsson et al. | 600/340 |
| 2007/0211925 A1 * | 9/2007 | Aoki et al. | 382/118 |
| 2007/0232930 A1 * | 10/2007 | Freeman et al. | 600/476 |
| 2008/0312552 A1 * | 12/2008 | Zhou et al. | 600/558 |
| 2011/0044549 A1 * | 2/2011 | Bressan | 382/225 |
| 2012/0093389 A1 * | 4/2012 | Halldorsson et al. | 382/134 |
| 2013/0324810 A1 * | 12/2013 | Gelland | 600/323 |

OTHER PUBLICATIONS

M Hammer et al., "Retinal vessel oximetry-calibration, compensation for vessel diameter and fundus pigmentation, and reproducibility", Sep. 2008, Journal of Biomedical Optics vol. 13(5), p. 1-7.*
J. Beach et al., "Oximetry of retinal vessels by dual-wavelength imaging: calibration and influence of pigmentation", Journal of Applied Physiology Published Feb. 1, 1999 vol. 86, p. 1-26.*
S. Hardarson et al., "Automatic Retinal Oximetry", Investigative Ophthalmology & Visual Science, Nov. 2006, vol. 47, No. 11, p. 5011-5016.*
J. Ramella-Roman et al, "Measurement of oxygen saturation in the retina with a spectroscopic sensitive multi aperture camera", 2008, Optics Express, vol. 16 No. 9, p. 1-13.*

* cited by examiner

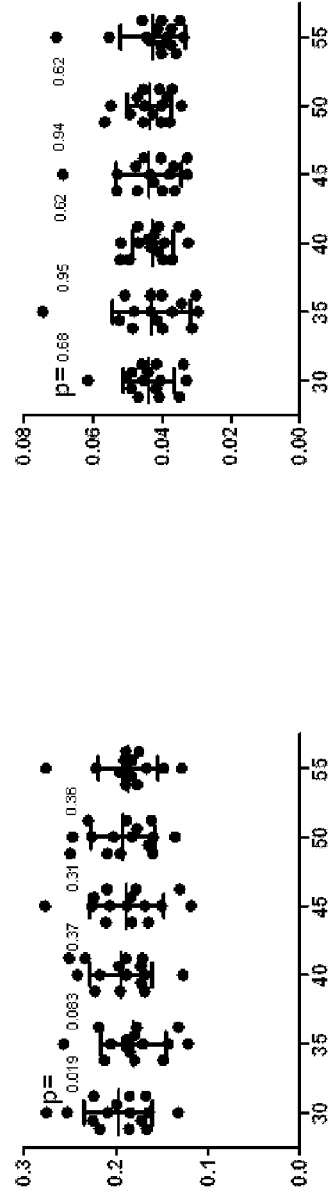
Figure 6
Figure 7
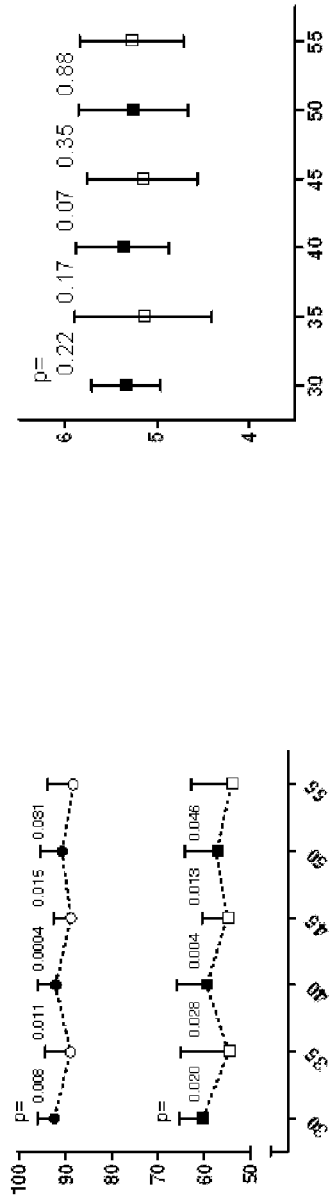
Figure 8
Figure 9

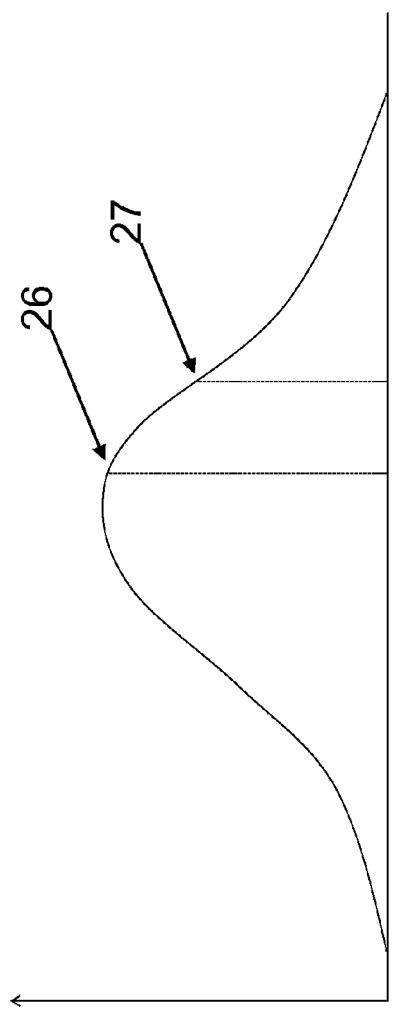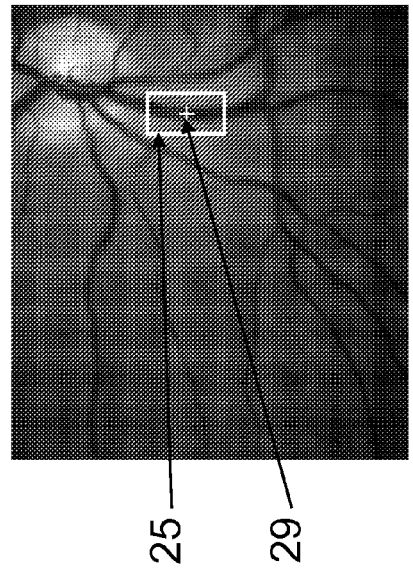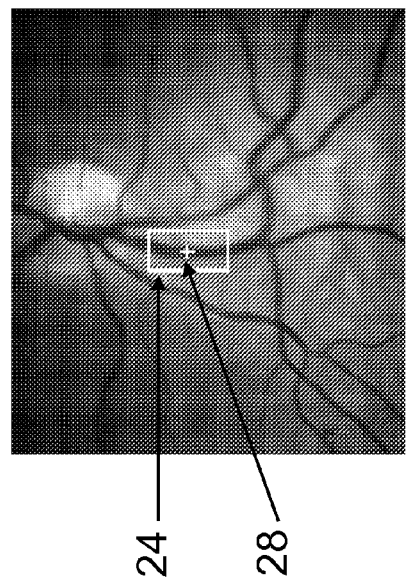

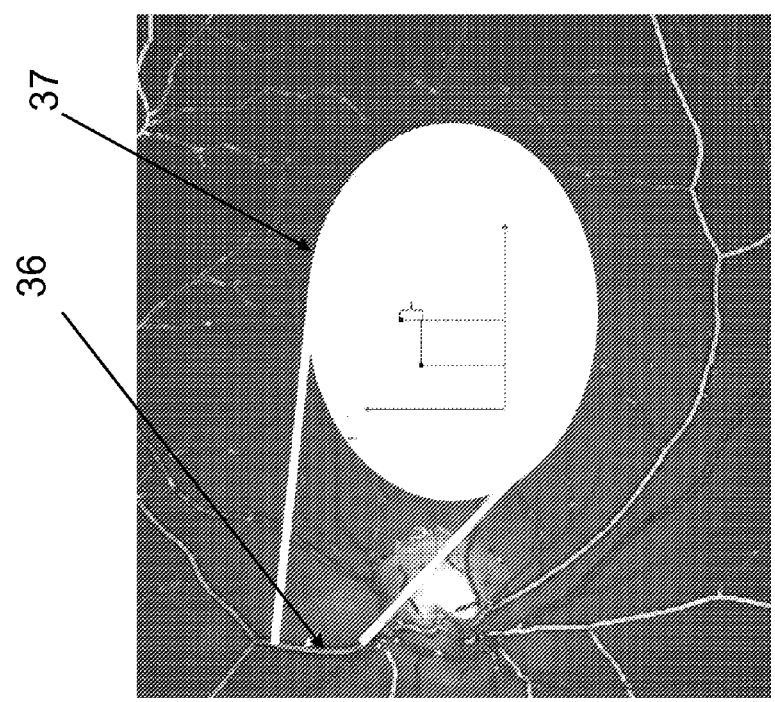
Figure 15
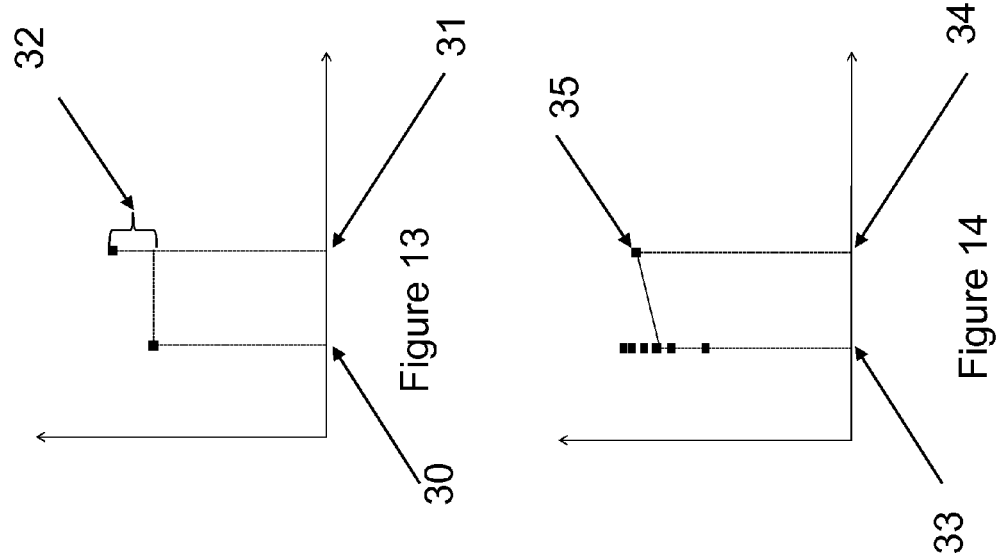
Figure 13
Figure 14

TEMPORAL OXIMETER

FIELD OF THE INVENTION

The present invention relates to a system for the measurement of oxygen saturation. The invention assists the comparison of two or more measurements.

BACKGROUND ART

Some of the disease states that pose the greatest danger to vision are thought to involve abnormalities in the oxygen supply to the retina or the oxygen metabolism. These include diseases such as diabetic retinopathy, which is one of the most common causes of blindness in the world, retinopathy of prematurity, retinal vein and artery occlusions. It has also been suggested that ocular blood flow is compromised in glaucoma, including normal tension glaucoma, and that the loss of optic nerve fibers in glaucoma patients may be due to ischemia. Age related macular degeneration may also involve ischemia and hypoxia.

The principle of spectrophotometric hemoglobin oximetry is old and the method has been developed into clinically useful instrumentation in several specialties of medicine. The finger or earlobe oximeter, commonly used in anesthesiology and intensive care is an example of the successful application of oximetry in medicine.

Information on retinal and optic nerve oxygenation in health and disease is mostly derived from animal research. Non-invasive measurement of oxygenation in the human retina and optic nerve has proved difficult but considerable progress has been made, particularly in recent years as digital technology has evolved. The potential use of retinal oximetry covers a range of areas, including assessment of oxygen metabolism in disease, the efficacy of treatment of these diseases in restoring or improving the metabolic conditions, either by laser treatment, surgery, lowering of intraocular pressure or by medication. Retinal oximetry may also be of use in elucidating further the physiological processes involved in disease states, such as in glaucoma and diabetic retinopathy.

In the 1990s, an important version of retinal vessel oximetry was developed at the University of Virginia, by James Beach and James Tiedeman. Their version was based on a method proposed by Delori with additional improvements. The main advantage of the Beach and Tiedeman method is the ability to obtain simultaneously two or more images of light reflectance at different wavelengths (called multi-spectral images) from the same fundus using a fundus camera. In this manner it is possible to record reflectance at both oxygen-sensitive and insensitive wavelengths from exactly the same area on the fundus, and at precisely the same time. This allows for precise quantification of the effects of oxygen binding on the light absorption spectra of hemoglobin. Oximetric measurements of this kind are achieved by a system whose main component consists of a modified fundus camera, although the internal xenon flash of the camera is still used as a light source, unmodified. Other components of the system are a beam splitter, a gray scale digital camera, possessing high quality linear performance, and a computer. The digital camera replaces the image acquisition mechanism of the fundus camera. Flashes from the fundus camera are synchronized with recordings by the digital camera electronically.

More sophisticated retinal oxymetry is disclosed in detail in US20060276698A1 patent application. The system is capable of automatically evaluating oxygen saturation of the optic nerve and retina. The system is comprised of an image capturing system which further comprises fundus camera, a beam splitter, a digital image capturing device, a computer system, image processing software performing in real-time the steps of registering a set of multi-spectral images. This is accomplished by binarizing multi-spectral image, finding all the border regions of each image by finding the region including the straight line that passes the highest number of points in the region. The orientation of the borders is used to evaluate the orientation of each spectral image, equalize the orientation of each spectral image by rotating the spectral image, edge detect each spectral image, and estimate the translation between the spectral images based on the edges of adjacent images. The images are then transformed to a stack of registered images, were blood vessels are located in each of the spectral images. The oxygen saturation level is finally evaluated, after sophisticated image processing, and the results are presented.

WO02080759 discloses retinal camera for examining an eye, the camera including a light source having first and second light sources for emitting first and second wavelength bands. The first and second light sources are arranged to alternately produce light onto the retina such that the absorptivity of light of the first wavelength band by oxygenated blood is greater than the absorptivity of light of the second wavelength band, and the absorptivity of light of the first wavelength band by the oxygenated blood is less than the absorptivity of light of the second wavelength band. Light is selectively focused from the first and second sources by an optical arrangement and imaging devices to produce respective images of a portion of the retina illuminated with the respective wavelength bands. The images obtained by the imaging device are processed by the imaging device and processor to determine a retinal metabolic image based on haemoglobin oxygenation. In an embodiment of the invention light is scanned across the retina.

This makes it possible for clinicians to evaluate the oxygen supply to the retina or the oxygen metabolism and the oxygen saturation of the retina and optic nerve. However, it would be extremely valuable to be able to compare successive measurements of the same optic nerve and retina.

SUMMARY OF THE INVENTION

The process of comparing two or more oximetry measurements is not trivial as there are several confounding factors that may complicate the comparison.

In the first aspect the present invention presents a method for detecting change in retinal oxygen saturation over time. The method comprises the steps of capturing a first group of images of two or more narrow band wavelengths, calculating oxygen saturation of a vessel in the first group of images, storing said first group of images on a data storage device, capturing a second group of images of two or more narrow band wavelengths, calculating the oxygen saturation of vessels in the second group of images, storing said second group of images on a data storage device, spatially registering the pair of the group of images, captured at different time and calculating the change in oxygen saturation.

In another aspect the present invention presents methods to detect the confounding factors affecting the measurements. The present invention also explains how to determine if the corresponding factors/parameters do affect the temporal comparison.

In another aspect the present invention gives a quantitative evaluation of reliability of the comparison by using optical density for quantification of image comparability.

This reliability parameter can then be used determine if comparison between oxygen saturation measurements at different points in time is valid.

In another aspect the present invention presents a computer program or suite of computer programs so arranged such that when executed on a processor said program or suite of programs cause(s) said processor to perform the methods discussed.

In another aspect the present invention discloses an apparatus for measuring change in oxygen saturation over time. The apparatus comprises a camera for capturing group of images of two or more wavelengths, a data storage device for storing the images, and a computer for receiving the group of images from the camera. The computer is furthermore adapted to preprocess the group of images, to detect vessels in the group of images, and to calculate the oxygen saturation in the group of images. The computer is furthermore adapted to spatially register a pair of the group of images captured at different time and to calculate the change in the oxygen saturation.

BRIEF DESCRIPTION OF FIGURES

FIG. 6: Optical density at an isobestic wavelength 586 nm ($OD_{586}$).
FIG. 7: Optical density independent of oxygen saturation and vessel width ($OD_{corr}$).
FIG. 8: Oxygen saturation in arterioles and venules.
FIG. 9: Vessel width of arterioles.
FIG. 10: Light distribution.
FIG. 11: Retinal image.
FIG. 12: Retinal image.
FIG. 13: Change in optical density.
FIG. 14: Multiple measurements taken during a single visit.
FIG. 15: Possible graphical representation of information.

DETAILED DESCRIPTION

Figure 1:
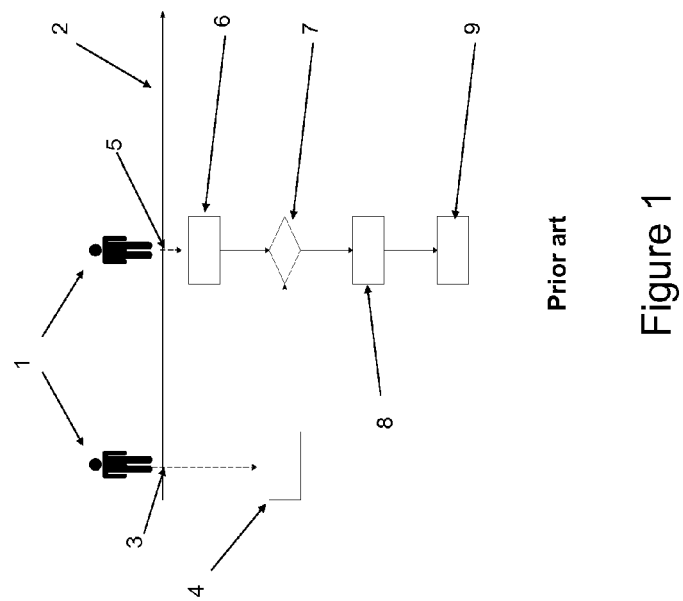
FIG. 1: Conceptual drawing of use.

This embodiment describes a process to help clinicians to determine if retinal oxygen saturation has changed over a series of two or more visits. FIG. 1 shows a typical scenario where a patient 1 comes for more than one visit (perhaps a part of a routine check) to see if there has been any change in the saturation level. The line 2 represents a timeline during which patient's treatment may take place. At time t1, 3 a first group of images at two or more wavelengths are captured, the images are processed and oxygen saturation evaluated 4 at the clinic and stored in a database. At a later time t2, 5 a second set of images 6 is captured and also stored in a database. The first and second set of images is compared in 7, and change in oxygen saturation is calculated 8. Finally, the effect of the treatment or progression of disease is represented in 9 and evaluated by clinician.

Figure 2:
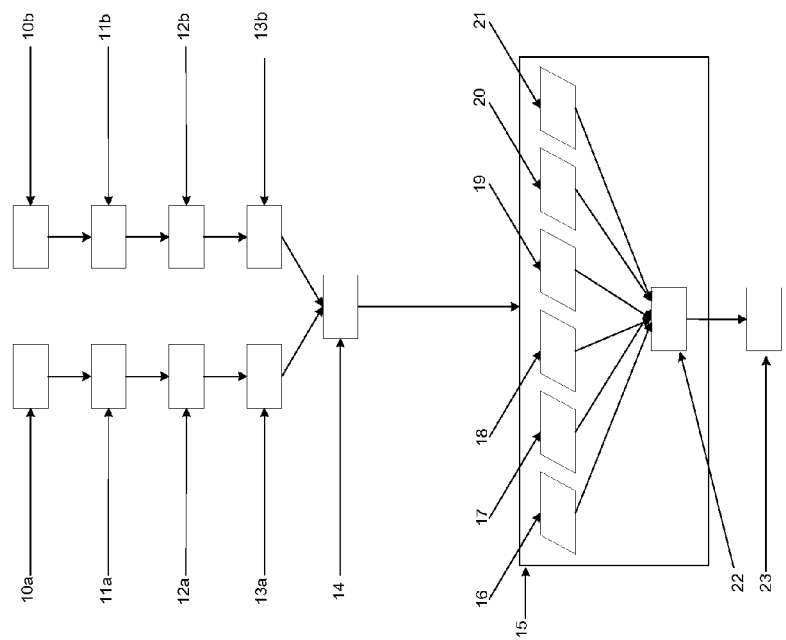
FIG. 2: Overall flowchart showing the process.

FIG. 2 illustrates the overall process. The patient comes in for the first visit and the first group of images are captured, 10a, the group of images is preprocessed 11a, and the vessels of interest are detected 12a. Next, the oxygen saturation is calculated 13a. Steps 10b-13b represent the same steps during the second visit. Now, to be able to reliably compare the oxygen saturation in the two separate groups of images the images must be spatially registered 14 and undergo a comparison quality test 15.

First, the two images are registered 14 together by evaluating transformation parameters that map features in the first image to corresponding features in the second image. The registration can be performed in a variety of manners to those skilled in the art. The quality comparison test measures several parameters to evaluate if the images are comparable. The same principle can of course be applied to a sequence of images consisting of plurality of images.

In one embodiment the optical density is measured at an oxygen insensitive wavelength and used for quantification of image comparability. The oxygen insensitive wavelength is also called isobestic wavelength and absorbance is same for oxygenated hemoglobin and de-oxygenated hemoglobin at such wavelengths. For each vessel, the optical density (OD) is measured as $OD=\log(I_0/I)$, where I is the measured light intensity at a vessel and $I_0$ is the original light or an estimate thereof. $OD_{ISO}$ is the optical density at isobestic wavelength and ODsens is optical density at an oxygen sensitive wavelength. It has been showed that the ratio ODR=ODsens/ODiso has shown to be linearly related to oxygen.

Figure 3:
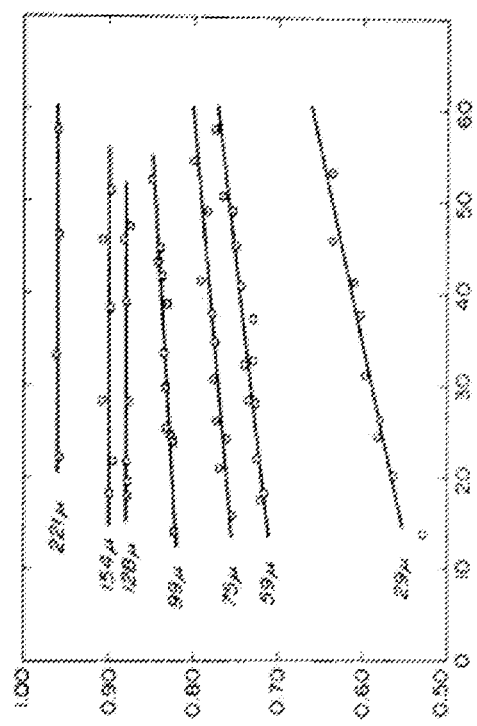
FIG. 3: Relationship between vessel width and hematocrit.

It has been proposed that $OD_{ISO}=e_{ISO}*C*d$, where $e_{ISO}$ is the extinction coefficient at the isobestic wavelength, C is the concentration of red blood cells in the blood (hematocrit) and d is the width of the vessel. Therefore, $OD_{ISO}$ changes with d and C but is independent of oxygen content. Hematocrit (hct) is proportion of blood volume occupied by red blood cell and is a linearly related to concentration of hemoglobin (cHb). In normal situations, hematocrit does not change greatly between measurements. However, in extreme cases it is known that hematocrit varies, in aneamia, such as in the case of renal failure. It has been shown that there is a relationship between vessel width and hematocrit, FIG. 3. FIG. 3 shows the Fahraeus effect; when blood flows from a reservoir into and through a small diameter tube, the average hematocrit in the tube is less than that in the reservoir. The tube's relative hematocrit is defined as the average hematocrit of the blood flowing through a tube divided by the hematocrit of the blood in the reservoir feeding the tube. The horizontal axis shows the reservoir hematocrit in %, the vertical axis the tube's relative hematocrit, and the numbers to the left of the lines are the tube diameters in micrometers.

Figure 4:
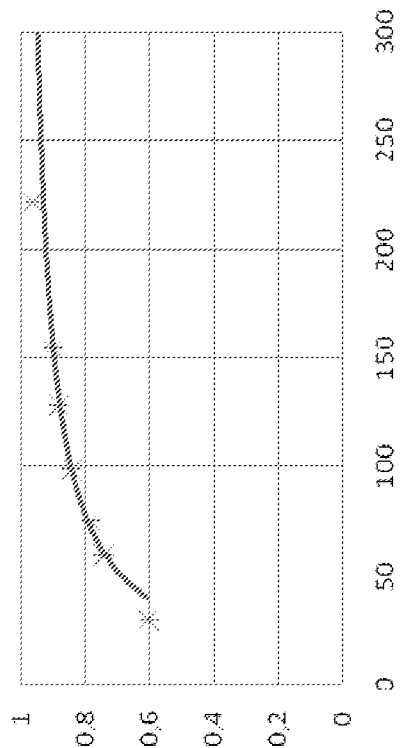
FIG. 4: Fitted measurements.

By fitting the measurements of FIG. 3, the relative change in hematocrit is estimated as: $h=1-a/d$, where d is vessel width, and the constant a is estimated $a=15.5$ μm, FIG. 4. The horizontal axis is the vessel width, d in micrometers while the vertical axis is the relative hematocrit as in FIG. 3. It is not known if the relationship between the concentration of blood and cHb can change temporarily. However, such change would be unlikely since this metabolic balance is very important for the human health. The blood is not a simple solution of hemoglobin and the scattering of light by erythrocytes may complicate the previous assumption. To be able to detect such complications a variable which is independent of both oxygen saturation and vessel width is defined as:

$OD_{corr}=OD_{ISO}/d*h$. Change in $OD_{corr}$ between measurements indicates that either blood concentration or scattering did change between measurements. These changes may affect the measurements of oxygen saturation because they are possibly dependent on wavelength and therefore changing the ratio of ODsens/$OD_{ISO}$ which ends up as an artificial change in oxygen saturation. Acceptable change in $OD_{corr}$ is estimated from the standard deviation of 5 repeated measurements in a population which is likely to be similar to standard users of the present invention, and defined as the mean standard deviation of $OD_{corr}$, $MstdOD_{corr}$. If it is assumed that $OD_{corr}$ is a Gaussian distributed variable, then there is less than 5% chance that change of more than $1.96*MstdOD_{corr}$ will occur. A change of more than $1.96*MstdOD_{corr}$ is therefore unlikely without any external complications. Preferably the change should be between 1-20% of $MstdOD_{corr}$, but more preferably between 2.5-10%, and most preferably 5%.

Figure 5:
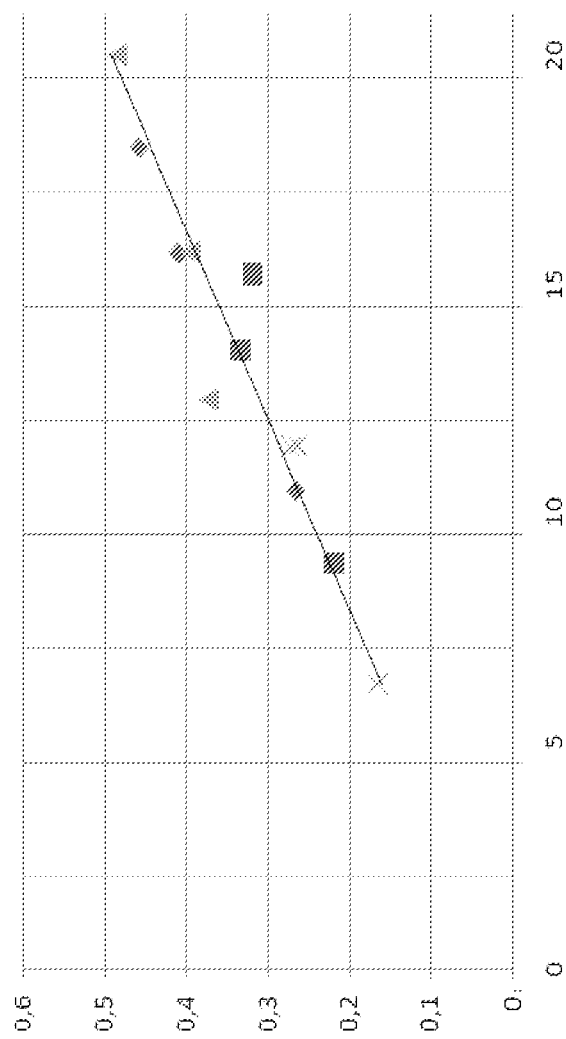
FIG. 5: Measurements from 4 vessel branches, vessel width vs optical density at an isobestic wavelength (570 nm).

If hematocrit changes between measurements it would affect the measurement of $OD_{corr}$ and trigger false alarm. One method to prevent such false alarm would be to measure the relationship of $OD_{ISO}$ and vessel width of all the vessels in the image (see FIG. 5). The slope between the two variables predicts the mean concentration of blood in vessels. If the concentration changed it may have been affected by temporary changes in hematocrit. By comparing the slope resulting from the vessels in the two images we can see if the slope (concentration) changed significantly. If that is the case the concentration of all the retinal vessels changed not only the concentration of an individual vessel. FIG. 5 shows the measurements from 4 vessel branches of one retinal image. The vertical axis is the optical density $OD_{ISO}$, and the horizontal axis is the vessel width in pixels, the diamond represents vein branch #1, the triangle vein branch #2, the square artery branch #1, and the artery branch #2. Each branch has 3 vessel (mother and two childs'), 6 arteries and 6 veins segments. There is a clear linear relationship between optical density on isobestic wavelength and vessel width since the coefficient of determination is $R^2=0.92$. Because the optical density at an isobestic wavelength is $OD_{ISO}=e_{ISO}*C*d$ the slope of the line is the measure of blood concentration.

The reliability of $OD_{corr}$ as a quality comparison parameter is established by the following experiment which shows that $OD_{corr}$ is constant although other external factors are changing. The data is from a study of the effect of light and dark environment on the retinal vessel oxygen saturation. Fifteen healthy individuals underwent oximetry measurements after being 30 minutes in the dark, followed by alternating 5 minute periods of white light (80 cd/m$^2$) and then dark again. The graphs in FIGS. 6 and 7 show the result of the study. The horizontal axis shows time of measurement. A measurement of oxygen saturation was made at the end of each period of light or dark. The P values pertain to comparison between successive measurements (paired t-tests). FIG. 6 shows the optical density at an isobestic wavelength, 586 nm, ($OD_{586}$) while FIG. 7 shows the optical density at the same wavelength independent of and vessel width, that is $OD_{corr}$.

FIG. 8 shows the saturation in arterioles and venules in the test while FIG. 9 shows the vessel width in arterioles. Again, the horizontal axis shows time of measurements. The results show that optical density at the isobestic wavelength changes between light and dark conditions. By correcting for vessel width, by calculating $OD_{corr}$, the change is no longer statically significant, FIG. 7, although the change in oxygen saturation between light and dark is statistically significant, FIG. 6. The stable reading of $OD_{corr}$ demonstrates the use of the parameter for predicting failure in the comparison of the oxygen saturation between two images taken at different time.

Other spectrophotometric technique use the optical density at more than two wavelength to determine oxygen. The method of calculating $OD_{corr}$ could also be used in these methods to evaluated a change oxygen saturation reliably.

In another embodiment the following test is executed to verify that changes in reflectance of the background are not affecting the oxygen saturation measurements, 17. To estimate the transmittance, $I_0$ in $OD=\log(I_0/I)$, the area around the vessel (both sides of the vessel) is filtered and averaged. The measured transmittance in the first image is $I1_{0,left}$ and $I1_{0,right}$, referring to the left and right side of the vessel, respectively. The process is then repeated for the second image and $I2_{0,left}$ and $I2\_0\_right$ are obtained. The ratio $I2_{0,left}/I1_{0,left}$ should not differ considerably from the ratio $I2_{0,right}/I1_{0,right}$. It is of course also possible to compare $I1_{0,right}/I1_{0,left}$ to $I2_{0,right}/I2_{0,left}$. Differences in these ratios indicate that background reflectance changes may have affected the reliability of the comparison. Changes in background reflectance may for example be caused by hemorrhages in the tissue which could artificially affect the measurement of vessel oxygen saturation.

In another enablement the change in texture rather than the average of the area is measured, 18. The texture changes may for example be calculated using entropy or standard derivation of the area but any other texture analysis method is intended to be covered by the claims of this patent. Both entropy and standard derivation estimate the texture variability of the area which may indicate that the retina is less pigmented and therefore the choroidal vessels are visible.

In another embodiment 19 the light distribution of the two images is evaluated, FIG. 10-12. If the illumination over the two images differs considerably the comparison of a vessel oximetry can become invalid. That is, if the same vessel is located in the area A1, 24, of the first image which has different illumination compared the area A2, 25, in the second image where the vessel is located. The two may not be comparable since the energy level at the area of interest is different. In the first image FIG. 11, the area of interest 24 is almost in the center of the image and hence receives high energy 26, FIG. 10. The second image, FIG. 12, is different. The area of interest 25 is of center and will, therefore, receive less energy 27, FIG. 10, simply because the light distribution over the field of view is Gaussian shaped and not homogeneous. The illumination properties of the system can be analyzed by capturing an image of a homogenous region. Say that we have this image h(x,y) stored. Then normalize the image so that mean value is one. To determine if the illumination is acceptable, it can be evaluated with the comparison $$\left| \frac{1}{n_1} \sum_{x,y \subset A1-A2} h(x,y) - \frac{1}{n_2} \sum_{x,y \subset A2-A1} h(x,y) \right| \le E,$$

where $n_1$ is number of pixels in area A1-A2, $n_2$ is number of pixels in area A2-A1 and E is the threshold for adequate difference of illumination. The threshold E may be in the range of 1.2-3, but more preferably 1.5-2.5, and most preferably 2.

In another embodiment 20, the center position of a corresponding vessel in the two original images FIGS. 11 and 12 is used for quality measurement. Say that the position of the vessel in the first image is P1 (x1,y1), 28, and the position of the same vessel in these second image is P2(x2, y2), 29, then the comparison with the Euclidean distance metric (it should be noted that any other suitable distance metric could be used) is $\|P1-P2\|=\sqrt{(x2-x1)^2+(y2-y1)^2} \le W$ where W is the suitable threshold and may be determined based on the zoom of the optical camera system (fundus camera) and the curvature of the retina. Range of W depends on zoom setting of the fundus camera and the size of the image sensor in pixels. For field of view (zoom) 50 degrees, W is preferably 1-8, more preferably 3-6, most preferably 4 optic disk diameters. A typical optic disk diameter is 1.5 mm on the retina. For field of view 35 degrees, W is preferably 1-6, more preferably 2-5, most preferably 3 optic disk diameter. For other zoom setting these calculations are straight forward.

Figure 16:
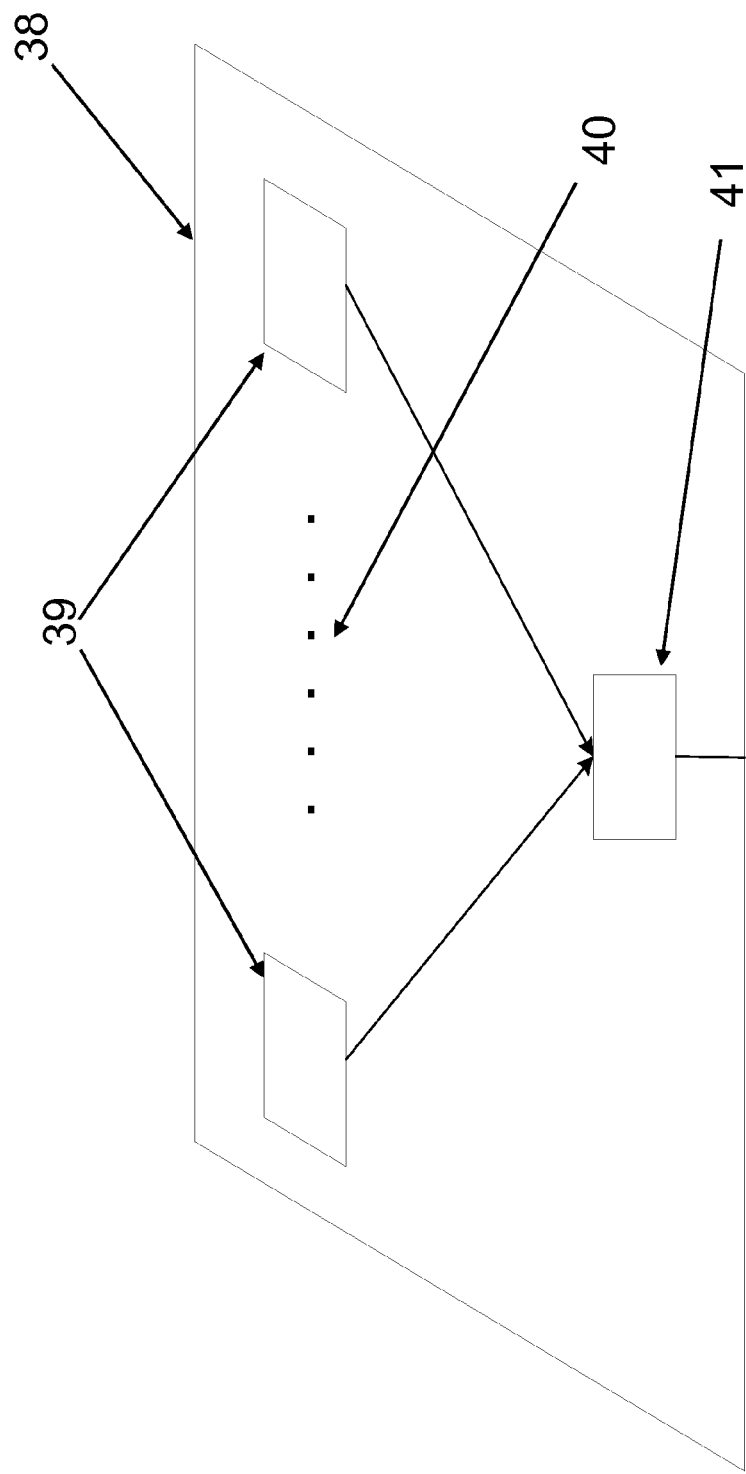
FIG. 16: Inside view of item 21, FIG. 2.

In another embodiment, the image quality is evaluated since the image quality may affect the result of measured oxygen saturation and therefore temporal comparison. There are different factors that characterize bad image quality such as: focus, reflection of the lens, and uneven illumination. A quantitative evaluation of image quality 21 may be used to reject images before comparison. Item 38, FIG. 16, represent the various image quality evaluation methods of box 21 from FIG. 2. It is difficult to develop one global parameter to quantify image quality based on a single method. However, it is possible to use several methods and combine their output using a weighting function 41. The quantitative evaluation of image quality, box 21 of FIG. 2, as shown in 38 represents any number 40 of image quality evaluation methods 39 as is shown in FIG. 16. Any single or combination of the following methods could be used but any other method capable of estimating image quality is intended to be covered by the claims of this patent.

Information Degradation:

Store the original image. Degrade the image such as by transforming it with a wavelet transform and quantize the wavelet coefficients and transform the image back. Then a similarity metric is used to measure the similarity between the original image and the degraded version. High similarity refers to little information lost during the degradation and therefore low quality image at the beginning.

Focus:

Can be estimated using contrast measurements (commonly used to autofocus).

Uneven Illumination:

Can be detected by applying a median filter to the image (to remove all features in the image such as vessels) and then analyze the image gradient and detect where it is steep.

Reflection of the Lens:

May be detected automatically as an extremely bright area of the image which often has a particular shape, which may be detected with morphological filters.

Shape of the Histogram:

The shape of the histogram can be an indicator of the information in the image and therefore the related to image quality. By compiling the intensity histogram of the image and use pattern classification it is possible to grade the quality of the image.

Each of the above described test and methods can disqualify the comparison of the two images. However, if none of the tests are optimal that might indicate a poor comparison quality. Thus, a weighted decision or a fuzzy decision or any other suitable mathematical functions model 22 may be more appropriate in some cases. Finally, the result of the change in oxygen saturation is presented to the user in step 23 of figure two. One main part of information obtained by the temporal oximeter is the change in oxygen saturation between two or more visits. FIG. 13 shows clearly how this can be measured and possibly presented to the user. The vertical axis shows the oxygen saturation while the horizontal axis shows the time. A visit date 30 is marked on the time axis and a second visit date 31 also. These two visits can be any two of many visits to the clinic. The difference in the oxygen saturation between those two visits is shown both visually and numerically 32 on the graph. Of course this information could be represented as text only, numerically only or graphically only. Moreover, there can be many appropriate ways of representing this information for example with a color coded map. Such variations of representation are intended to be covered by the claims of this patent.

FIG. 14 shows the case were multiple measurements 33 are taken during the same visit to the clinic, measurement 35 taken at a later time could be compared to the mean of the multiple measurements taken at the previous visit. For a person skilled in the art, there are many other algorithms to select the two images.

In one embodiment, multiple images are taken at each visit. A composite image is created from the multiple images taken at each visit and the resulting composite images from successive visits are compared.

FIG. 15 shows yet another way of representing the measurement information. The user selects a vessel to inspect in the image and a bubble or a box with the relevant information is presented.

The invention claimed is:

1. A method for detecting change in retinal oxygen saturation over time, said method comprising the steps of:
    capturing a first group of retinal images of two or more narrow band wavelengths, wherein at least one of said narrow band wavelengths is at one or more isobestic wavelengths, by means of camera;
    measuring optical density of one or more areas of interest in the first group of retinal images;
    determining oxygen saturation in said first group of retinal images;
    storing said first group of images on a data storage device;
    capturing a second group of retinal images of two or more narrow band wavelengths, wherein at least one of said narrow band wavelengths is at one or more isobestic wavelengths, by means of camera;
    measuring the optical density of one or more areas of interest in the second group of retinal images;
    storing said second group of retinal images on a data storage device;
    determining oxygen saturation in said second group of retinal images,
    said first group and second group of retinal images, captured at different times, are spatially registered, by mapping features in the first group of images to the corresponding features of the second group of images; and
    detecting a change in retinal oxygen saturation between said first group of retinal images and said second group of retinal images;
    evaluating image comparability of said first and second groups of images captured at said one or more narrow band wavelengths, to determine if comparison between retinal oxygen saturation measurements at different point in time is valid, by comparing said optical density between said first and second groups of retinal images, wherein the step of evaluating image comparability comprises the steps of:
    measuring the optical density of said first and second groups of retinal images at one or more isobestic wavelength;
    scaling said optical density according to vessel width; and measuring the difference of said scaled optical density between said first and second groups of retinal images by calculating the difference of said optical densities.

2. The method according to claim 1, wherein said quantized image comparability further comprises the steps of:
measuring relative change in hematocrit; and
scaling said optical density according to vessel width and relative change in hematocrit.

3. The method according to claim 1, wherein said isobestic wavelength is a narrow band wavelength centered around said isobestic wavelength.

4. The method according to claim 1, wherein said evaluating image comparability comprises the steps of:
measuring the background reflectance of said first and second groups of retinal images by filtering and averaging the background; and
measuring the changes of said background reflectance between said first and second groups of retinal images by calculating the ratio of said background reflection.

5. The method according to claim 4, wherein said changes in background reflectance comprises the step of:
measuring the background reflection on either side of said vessel calculating the ratio of said background reflection on either side of the vessel.

6. The method according to claim 4, wherein said changes in background reflectance comprises the step of:
measuring change in texture on either side of said vessel by calculating texture variability of the area on either side of said vessel.

7. The method according to claim 1, wherein said evaluating image comparability comprises the step of:
measuring the vessel shift distance between successive groups of images, by applying distance metric.

8. The method according to claim 1, wherein said evaluating image comparability comprises the step of:
using one or more image quality parameters to reject images.

9. The method according to claim 8, wherein said evaluating image quality parameter comprises the steps of:
measuring the information degradation of said images, by degrading each image with wavelet transformation function;
quantizing wavelets coefficients;
transforming the image back;
measuring the similarity between original and degraded image.

10. The method according to claim 8, wherein said evaluating image quality parameter comprises the step of:
measuring the focus of said images by applying contrast measurements.

11. The method according to claim 1, wherein said change in optical density is used to calculate change in parameters derived from the optical density.

12. The method according to claim 11, wherein said change in parameters derived from optical density is the difference between the parameters derived from the optical density level calculated from the said pair of groups of images captured at different time.

13. The method according to claim 11, wherein standard deviation of population similar to the one being measured is used to determine if the said change in the parameters derived from the optical density is statistically significant change.

14. The method according to claim 11, wherein said parameter is oxygen saturation.

15. A computer program or suite of computer programs embodied on a non-transitory computer readable medium, and so arranged such that when executed on a processor said program or suite of programs cause(s) said processor to perform a method comprising the steps of:
measuring optical density of one or more areas of interest in a first group of captured retinal images of two or more narrow band wavelengths, wherein at least one of said narrow band wavelengths is at one or more isobestic wavelengths;
determining oxygen saturation in said first group of retinal images;
storing said first group of retinal images on a data storage device;
measuring the optical density of one or more areas of interest in a second group of captured retinal images of two or more narrow band wavelengths, wherein said at least one of said narrow band wavelengths is at one or more isobestic wavelengths;
storing said second group of images on a data storage device;
determining oxygen saturation in said second group of retinal images;
spatially registering the said first and second group of retinal images, captured at different times, by mapping features in the first group of images to the corresponding features of the second group of images;
detecting the change in retinal oxygen saturation between said first group of retinal images and said second group of retinal images; and
evaluating image comparability of said first and second groups of images captured at said one or more narrow band wavelengths, to determine if comparison between retinal oxygen saturation measurements at different point in time is valid, by comparing said optical density between said first and second groups of retinal images, wherein the step of evaluating image comparability comprises the steps of:
measuring the optical density of said first and second groups of retinal images at one or more isobestic wavelength;
scaling said optical density according to vessel width; and
measuring the difference of said scaled optical density between said first and second groups of retinal images by calculating the difference of said optical densities.

16. A non-transitory computer readable data storage medium storing the computer program or at least one of the suites of computer programs of claim 15.

17. A computer program product according to claim 15, wherein a database resides on the same computer as said computing program product.

18. A computer program product according to claim 15, wherein a database, and said computing program product reside on different computers.

19. An apparatus for measuring change in retinal oxygen saturation over time, said apparatus comprising:
a camera, wherein said camera is adapted to capture a group of retinal images of two or more narrow band wavelengths, wherein at least one of said narrow band wavelengths is at one or more isobestic wavelengths;
a data storage device;
a computer, wherein said computer is adapted to receive said group of retinal images from said camera and stores said group of retinal images on said data storage device;
said computer is furthermore adapted to calculate the optical density and determine oxygen saturation in said group of retinal images;

said computer is adapted to spatially register a first group and a second group of retinal images captured at different time, by mapping features in the first group of images to the corresponding features in the second group of images, wherein said computer is adapted to evaluate comparability of said first and second group of retinal images based on said optical density, and determine if comparison between oxygen saturation measurements at different point in time are valid, by comparing said optical density between the first and second groups of retinal images, at said one or more isobestic wavelength, and wherein said computer is further adapted to:
  measure the optical density of said first and second groups of retinal images at one or more isobestic wavelength;
  scale said optical density according to vessel width; and
  measure the difference of said scaled optical density between said first and second groups of retinal images by calculating the difference of said optical densities.

\* \* \* \* \*